United States Patent [19]
Wirt et al.

[11] 3,960,004
[45] *June 1, 1976

[54] METHOD FOR MEASURING IMPEDANCE

[75] Inventors: Leslie S. Wirt, Newhall; Duane L. Morrow, Saugus, both of Calif.

[73] Assignee: Lockheed Aircraft Corporation, Burbank, Calif.

[ * ] Notice: The portion of the term of this patent subsequent to July 23, 1991, has been disclaimed.

[22] Filed: June 18, 1974

[21] Appl. No.: 480,555

Related U.S. Application Data

[63] Continuation-in-part of Ser. No. 245,776, April 20, 1972, Pat. No. 3,824,842.

[52] U.S. Cl. .................................... 73/67.1; 73/69; 324/57 R; 324/57 SS
[51] Int. Cl.² ......................................... G01N 29/00
[58] Field of Search ............... 73/67, 67.1, 69, 555; 324/58 B, 58.5 B, 57 R, 57 H, 57 SS

[56] References Cited
UNITED STATES PATENTS

| | | | |
|---|---|---|---|
| 1,816,917 | 8/1931 | Smythe et al. | 73/67.1 X |
| 2,043,984 | 6/1936 | Alder | 73/69 |
| 2,680,837 | 6/1954 | Sensiper | 324/58 |
| 2,970,258 | 1/1961 | Sinclair | 324/57 R |
| 3,771,057 | 11/1973 | Persidok | 324/57 R |

*Primary Examiner*—Richard C. Queisser
*Assistant Examiner*—John P. Beauchamp
*Attorney, Agent, or Firm*—Billy G. Corber; Ralph M. Flygare

[57] ABSTRACT

Apparatus and method for measuring the impedance of oscillatory systems, or elements of such systems, which exhibit nonlinear behavior at high excitation amplitudes. Excitation of the element being tested, which element may be either acoustical, electrical, or mechanical, is in the form of a combination of a high-intensity biasing signal having a broadband spectrum, and a low-intensity pure sinusoidal tracer signal. The tracer signal is retrieved at an appropriate measuring point in the test system by means of highly-selective filtering. Although the broadband signal comprises the real or basic test signal input to the test element, the retrieved tracer signal is substituted therefor for the purpose of deriving the element's impedance through the use of conventional impedance algorithms. Algorithm solutions thus provided correspond to the response of the element to the entire spectrum of the broadband excitation.

3 Claims, 9 Drawing Figures

FIG. 7 : PRIOR ART

METHOD FOR MEASURING IMPEDANCE

CROSS-REFERENCE TO RELATED APPLICATION

This is a continuation-in-part of our copending patent application, Ser. No. 245,776, filed Apr. 20, 1972, entitled "Apparatus and Method for the Measurement of Acoustic Absorption and Impedance," now U.S. Pat. No. 3,824,842.

BACKGROUND OF THE INVENTION

This invention relates to the measurement of certain functional properties of acoustical, mechanical, or electrical systems, or elements of such systems, and more particularly, to an apparatus and method for measuring certain functional properties of that class of oscillatory systems which exhibit nonlinearity of frequency response with changes in the amplitude of excitation of the system. As is well known to those versed in the art, analogies can be made in many instances between mechanical, acoustical, and electrical systems or devices. An electrical circuit can be considered to be a vibrating system, and this immediately suggests analogies between electrical circuits and vibrating systems. Frequently, electrical network analogs are employed in the design of mechanical systems, acoustical devices, and combinations thereof. The analogies between mechanical, acoustical, and electrical impedances are useful in the solution of many design problems because it permits the analysis to be conducted by the equations of electrical circuits. This design methodology is explained in detail in the book "Dynamical Analogies" by Harry F. Olson, published in 1958. Further reference to this subject may be had in the "McGraw-Hill Encyclopedia of Science and Technology" (1966 Edition) under the subject heading "Dynamical Analogies."

It is frequently desirable to obtain the characteristic impedances of various dynamic or oscillatory systems in order to design or improve devices incorporating such systems. Acoustic impedance, as conventionally defined at a given surface, is the complex ratio of effective sound pressure averaged over the surface to the effective flux (volume velocity or particle velocity multiplied by the surface area) through it. The unit is the newton-second/meter$^5$, or the mks acoustic ohm. In the cgs system the unit is the dyne-second/centimeter$^5$. Acoustic impedance, being a complex quantity, can have real and imaginary components analogous to those in electrical impedances.

For a system executing simple harmonic motion, mechanical impedance is defined as the ratio of force to particle velocity. If the force is that which dries the system and the velocity is that of the point of application of the force, the ratio is the input or driving-point impedance. If the velocity is that at some other point, the ratio is the transfer impedance corresponding to the two points. As in the case of electrical impedance, to which it is analogous, mechanical impedance is a complex quantity. The real part, the mechanical resistance, is independent of frequency as the dissipative forces are proportional to velocity; the imaginary part, the mechanical reactance, varies with frequency, becoming zero at the resonant and infinite at the anti-resonant frequencies of the system.

The total opposition that an electrical circuit presents to an alternating current comprises impedance. Electrical impedance is frequently defined as the ratio of the root-mean-square (rms) voltage to the rms current. Dynamic or oscillatory systems of the type herein considered may comprise either acoustical, electrical, or mechanical elements (or combinations thereof) all of which may have generally similar impedance analogies. Heretofore, various means and methods have been proposed for making impedance measurements in such systems. A consideration of acoustic impedance measurement techniques will serve to exemplify the background of the present invention. A widely accepted technique of the prior art for the measurement of acoustical impedance (and/or absorption coefficient) involves the use of a standing-wave tube. Standards for such tubes have been set forth by the American Society for Testing Materials and are described in "Standard Method of Test for Impedance and Absorption of Acoustical Materials by the Tube Method," (ASTM Designation: C 384–58, 1958 - ASTM Std., Part 5, 997–1009, 1961).

In general, prior art methods, including the ASTM standard test, make the tacit assumption that the quantities being measured are functions of frequency but are independent of the intensity of the (sinusoidal) test signal. That is to say that it is assumed that the material is linear in its acoustical behaviour. More recently, when such measurement methods are applied to materials known to be nonlinear, the intensity of the test signal sometimes has been stated as a test condition.

It has now been discovered experimentally that the nonlinearity of an acoustical material has a further consequence. Specifically, if the use of a particular sinusoidal test signal results in the observation of an acoustic impedance $Z_1$ at frequency $F_1$, then the superposition of additional sound at frequencies other than $F_1$, such as for example broadband noise, causes the impedance to change to some value $Z_2$ even though all measurements are made at the original frequency $F_1$ only. The more nonlinear the material being tested, the more pronounced this effect becomes. Thus, the impedance at each frequency $F_1$ is a function of both the level and the spectrum shape of the entire noise present in the material's environment and if the level of a pure tone at $F_1$ is less than the overall level of the rest of the noise spectrum then the measured impedance becomes independent of the level of the sinusoidal signal at the frequency $F_1$. This discovery requires the modification of the more usual definition of acoustical impedance to include a statement of the acoustical environment to which the material is exposed.

The present invention, as will be described below, provides a means for modifying and adapting the standard test apparatus and method to conveniently measure acoustic impedance in accordance with the revised definition. As suggested above, the invention similarly extends to, and covers, the analogous disciplines of mechanical and electrical vibratory or oscillatory systems wherein mechanical impedance, or, as the case may be, electrical impedance, can be correctly measured notwithstanding the existence of non-linear response characteristics of the element being measured which would otherwise introduce error into the desired measurement.

It is recognized that prior attempts have been made to calculate the impedance of nonlinear system elements in the presence of noise. The problem involves the mathematical intractibility which characterizes nonlinear systems. In principle, however, it is solvable at least by successive approximation. The novel and improved method of the present invention provides a practical means for experimentally checking such analyses.

BRIEF SUMMARY OF THE INVENTION

The method of the present invention comprises injecting a pure tracer signal into a high-intensity, shaped, random-noise spectrum which is then propagated into the oscillatory system, or system element, for which an impedance measurement is sought. The pure tracer signal is retrieved from the mixture of the pure tracer signal and the broadband high-intensity noise signal, via a narrow-band tracking filter. The extracted tracer signal corresponds to the phase-angle signal employed in conventional impedance-measuring techniques. The desired impedance measurement is derived from the well-known analytic relationship of the data thus obtained from the system.

Thus, there is provided by the present invention means for obtaining acoustical, mechanical, or electrical impedances of nonlinear oscillatory systems, driven at high amplitudes into their nonlinear regime, which impedances could not otherwise be correctly determined. A consequence of the invention is that it has been shown that conventional procedures for the operation of high-intensity standing wave apparatus for acoustic measurements are inadequate in that they cannot provide a definition of material characteristics suitable for insertion into the wave equation as boundary conditions. Similar discrepancies exist in the analogous electrical and mechanical disciplines. In accordance with the present invention, as it applies to nonlinear systems, the word "impedance" is redefined as follows: the impedance of a nonlinear oscillatory system element is the ratio of force (or rms voltage) to the normal component of the particle velocity (or rms current), appearing in the system element, at a particular frequency, and in the presence of a specified excitation spectrum.

DETAILED DESCRIPTION OF THE PREFERRED EMBODIMENTS

Figure 1:
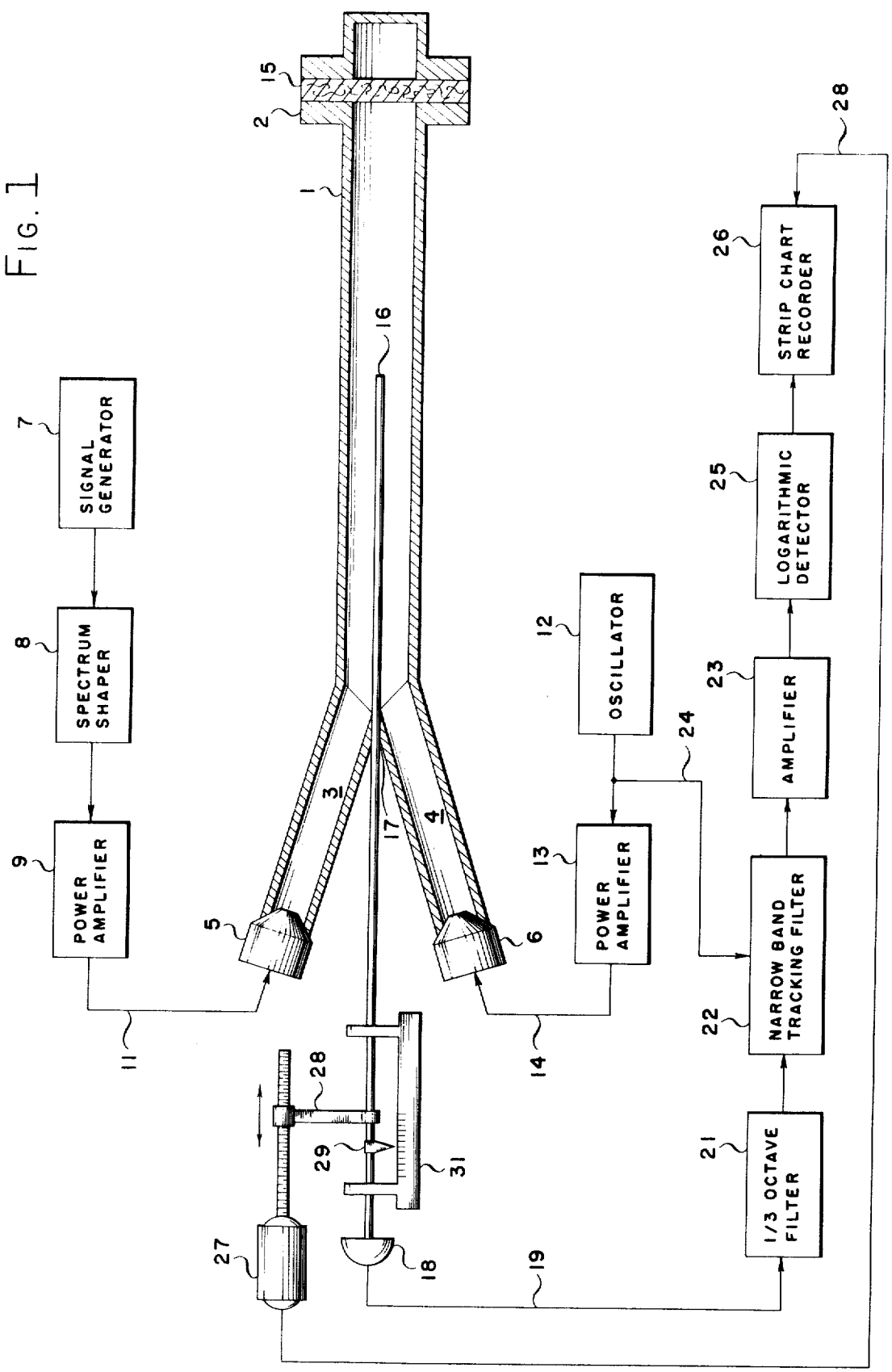
FIG. 1 is a block diagram of an embodiment of the invention as applied to the field of acoustics.

The present invention is based upon the discovery that given any system subjected to a dynamic (oscillatory) excitation, be it an electrical voltage, an acoustical pressure, or a mechanical force or mechanical torque, if its impedance (complex ratio of excitation to response) is not constant with amplitude of excitation force at any given frequency, then the usual test methods using sinusoidal test excitation forces (or voltages, or pressures) yield usually erroneous results. The results obtained are valid only for applications which subject the device to exactly the same excitation as the test signal used. If, as is more usually the case, the excitation contains significant components at other frequencies, then the impedance at the test frequency differs from that observed in the single frequency test. This difficulty is obviated by the present invention, which provides for the measurement of impedance at any desired frequency in the presence of the excitation expected in the actual application. As indicated previously, a complete set of acoustical-electrical-mechanical analogies exist such that acoustical and mechanical vibration problems may be formulated and solved in terms of analogous electrical circuits. The basic analogies are as shown below:

| Analogous Quantities and Commonly Used Symbols | | |
|---|---|---|
| Electrical | Mechanical | Acoustical |
| Voltage V | Force F | Pressure P |
| Current I | Velocity V | Volume Velocity U |
| Resistance R | Resistance R | Resistance R |
| Inductance L | Mass M | Inertance L |
| Capacitance C | Compliance C | Capacitance C |
| Impedance Z | Impedance Z | Impedance Z |
| Reactance X | Reactance X | Reactance X |

Equations defining impedance are as follows:

| Electrical | Mechanical | Acoustical |
|---|---|---|
| $Z = \frac{V}{I} = R + jX$ | $Z = \frac{F}{V} = R + jX$ | $Z = \frac{P}{U} = R + jX$ |

The method of the invention, as applied to the field of acoustics, comprises the measurement of acoustical impedance and absorption coefficients of various materials, and particularly those materials comprising the class which exhibit nonlinear behavior at high intensities of sound. Apparatus constructed in accordance with the invention and which is useful in carrying out the method of the invention, is illustrated schematically in FIG. 1.

An elongated tubular chamber, comprising tube 1, is closed at one end by means of termination 2. The opposite end of the tube 1 is provided with waveguides 3 and 4 which may be of exponential flare or other suitable shape. Electroacoustic driver unit 5 is coupled to throat 3, and electroacoustic driver unit 6 is coupled to throat 4. In the interest of clarity only two driver units, 5 and 6, and their respective throats 3 and 4, are shown in the drawing. However, in a practical construction it is preferred that four such driver units and horns be coupled to the standing-wave tube 1 in order to effectively handle the desired acoustic power levels. To minimize phase cancellation among the several driver units, the waveguides (3 and 4) converge at a minimal angle of about 9° from the axis of the measuring section comprising tube 1. It is preferred that the convergence angle of waveguides 3 and 4 not exceed approximately 30° from the major axis of the chamber. Each driver unit (e.g., 5,6) is energized from its own power amplifier.

A signal generator 7, comprising a broadband noise source, has its output supplied to a spectral shaper 8 to yield a broadband noise signal shaped to resemble that of the noise encountered in the normal operating environment of the test specimen. Spectrum shaper 8 may be selectively adjustable with respect to the noise spectra and level desired for any given test specimen. The shaped broadband noise signal is amplified by power amplifier 9 and used to energize driver unit 5. The signal on line 11 comprises the high-intensity biasing noise and is designated by spectrum shape and overall level. In a typical application, the broadband noise propagated into the chamber is at an overall level greater than 100 decibels, where 0 decibels equals 0.0002 dyne per square centimeter. In almost all practical applications of acoustic materials to high-intensity sound problems, the actual noise comprises many frequencies and is commonly broadband noise. It is preferred that three driver units, such as the single unit indicated at 5, and their ancillary amplifiers be used in combination to supply the high-intensity broadband noise to the standing wave tube 1.

Sinewave oscillator 12 provides a pure sinewave tracer tone which is amplified by power amplifier 13 and supplied to driver unit 6. Since the pure sinusoidal tone is at a level which is always low as compared to the overall sound intensity propagated into tube 1 by the broadband noise source, only a single driver unit 6 need be employed for this purpose.

While the described embodiment utilizes separate driver units and associated amplifiers for the tracer signal and the biasing signal, it should be understood that the tracer signal could be electronically mixed with the biasing signal and supplied to a single driver unit of appropriate power-handling capability.

The test specimen 15 is interposed between termination 2 and the specimen-receiving end of tube 1. It is preferred that the surface area of the specimen 15 equal the cross sectional area of the impedance tube 1. A small microphone or slender, hollow probe tube 16 is movably disposed on the axis of the measuring tube 1. A seal 17 is provided at the sound input end of tube 1, through which probe 16 extends. The movable probe 16 is connected to a pressure microphone 18 which supplies an output signal on line 19 to ⅓ octave filter 21.

Filter 21 is cascaded with a narrow-band tracking filter 22, having a bandwidth, in a typical construction, of 1.8 Hertz (Hz). To facilitate tracking, it is preferred that the narrow-band filter 22 have a selectively adjustable center frequency. Cascaded filters 21 and 22 accomplish the retrieval of the tracer sinewave signal which is then supplied to amplifier 23. In order to overcome any possible instability of oscillator 12, a narrow-band tracking filter 22 may be used which is tuned by the pure tone tracer signal itself via line 24 from oscillator 12. The amplified tracer signal is supplied to logarithmic detector 25, the output of which is used to drive strip chart recorder 26.

The motor 27 and lead-screw mechanism 28 assembly mechanically drives or translates probe 16 along the axis of the measuring section of tube 1 in order to sense the maxima and minima of the standing-wave pattern within the tube. That is, the sound pressure at the tip of the probe 16 will be sensed and converted into an electrical signal which is ultimately converted to a plot on the strip chart recorder 26. The translation of the probe, by motor 27, is synchronized with the chart feed of recorder 26 to provide the desired amplitude-versus-position plot. Displacement of the probe may also be observed directly by means of pointer 29 and scale 31. The absorption coefficient, acoustic impedance, acoustic resistance, and other parameters of the specimen, are calculated from the position and relative magnitude of the minima and maxima of the standing wave pattern in the tube, as will be readily understood by those skilled in the art. Reference may be had to "Acoustical Engineering" by Harry F. Olson (D. Van Nostrand Company, Inc.), Second Edition, pgs. 383–384, for a description of the derivation of sound absorption coefficient, acoustical resistance, acoustical reactance, and acoustical impedance from measured data. The relevant subject matter of the foregoing publication, "Acoustical Engineering," is incorporated herein by reference.

In a typical construction, microphone 18 may comprise a condenser microphone acoustically coupled to probe 16.

Figure 2:
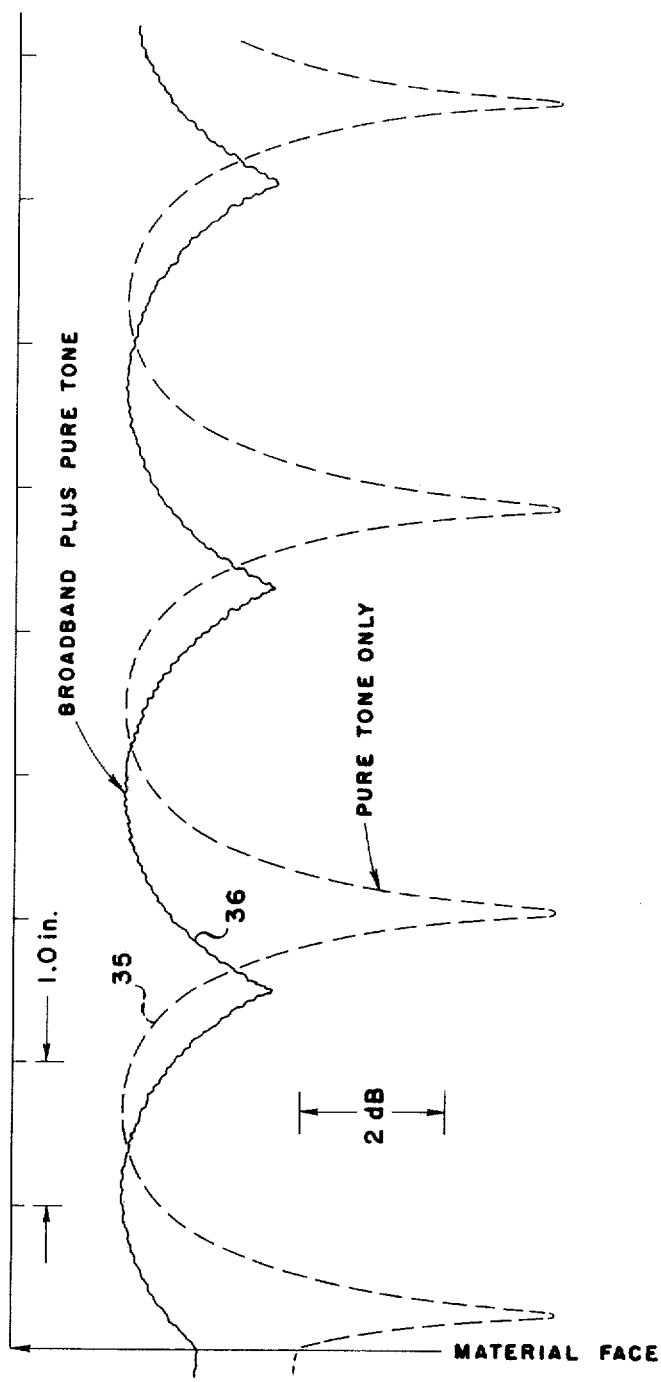
FIG. 2 illustrates graphically the standing-wave patterns observed in the presence and absence of broadband bias noise.

There is shown in FIG. 2 the superposition of tyical strip chart recordings made by the conventional method (viz., sinewave test signal only), as indicated by line 35, and by the method of the present invention (viz., low-level sinewave tracer signal plus high-level broadband bias signal), as indicated by line 36. Note the changes in both the location of the minima and the level of the minima. The impedance and absorption coefficients calculated from the two traces differ considerably. Tests made using the method of this invention at different levels of the broadband noise show similar differences. This indicates that both the spectrum shape and the level of the broadband noise must be stated as a test condition. On the other hand, once the broadband noise is present, the level of the sinusoidal tracer signal may be varied over a wide range without significantly changing the test results so long as the level of the tracer is kept less than the overall level of the broadband noise.

Figure 3:
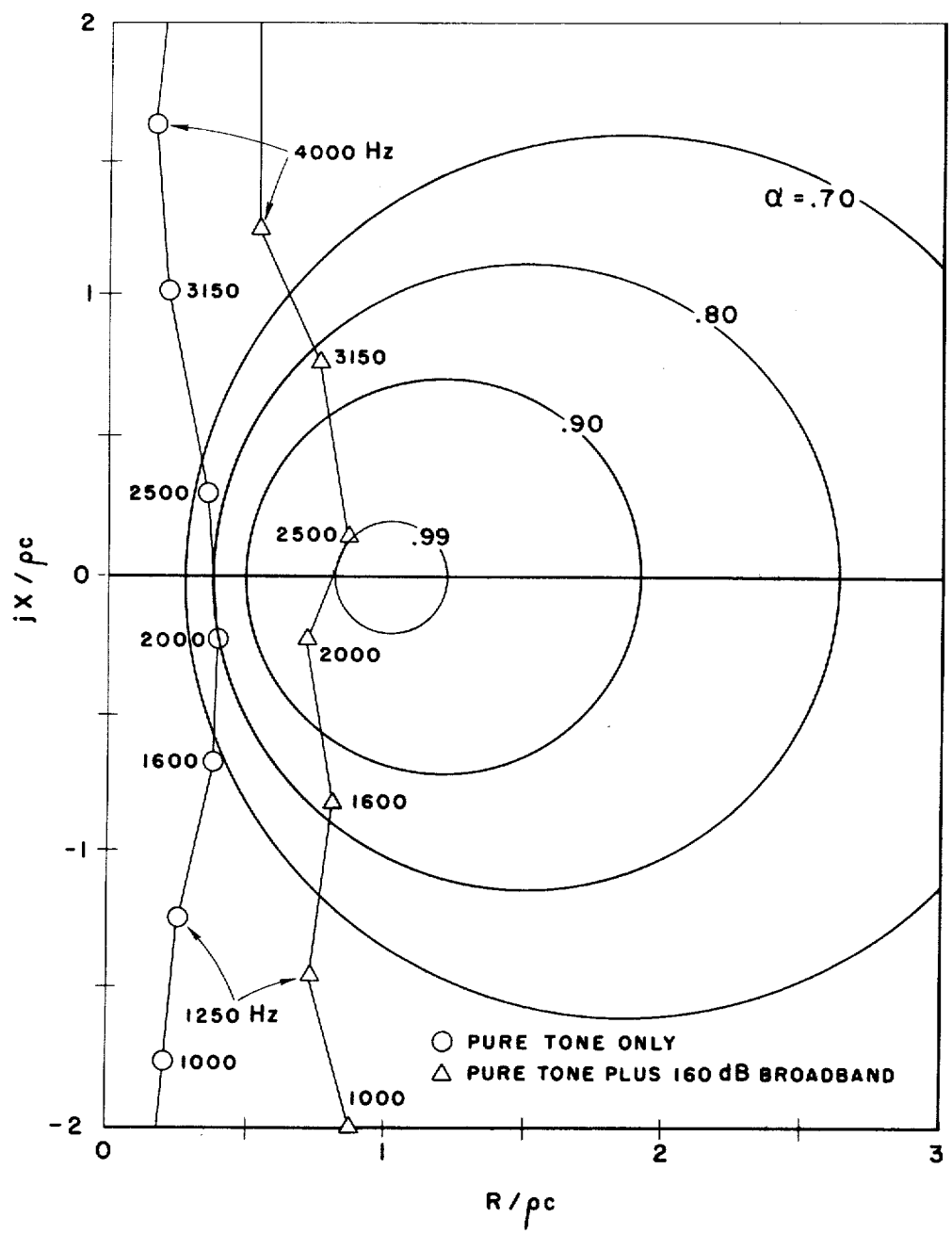
FIG. 3 illustrates graphically the impedances obtained from a first test sample in accordance with the method of the invention, and those obtained by prior methods.
Figure 4:
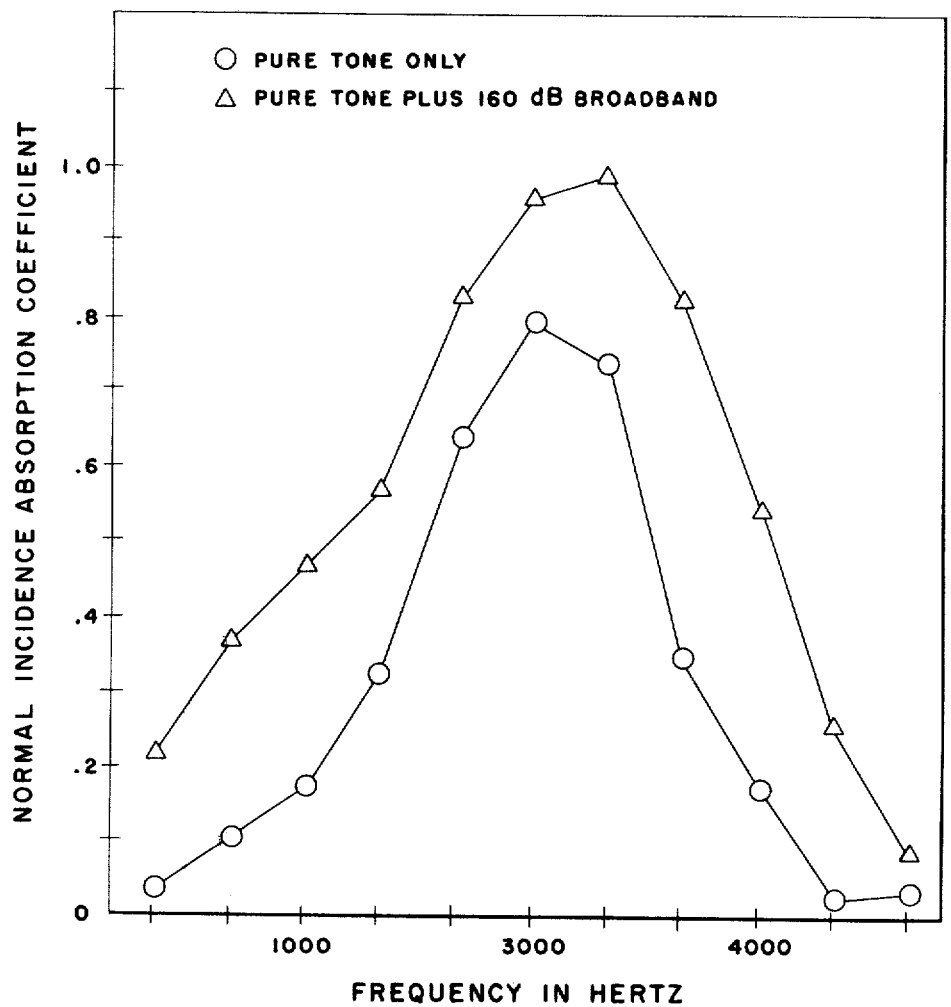
FIG. 4 is a graphic diagram illustrating the absorption coefficients of the sample referred to in FIG. 3.

FIG. 3 illustrates the dramatic change in impedance loci that results from the presence or absence of the broadband noise in the case of a test specimen comprising a typical perforated material. The coordinate axes are normalized by the characteristic impedance $\rho c$ where $\rho$ is the fluid density and $c$ is the velocity of sound; $\rho c = 42$ c.g.s. units for room temperature air. The non-concentric circles are contours of equal absorption coefficient. With their aid the absorption coefficients may be read directly from the impedance plots. Absorption coefficient is related to impedance by the relation:

$$\alpha = \frac{4 \frac{R}{\rho c}}{\left(\frac{R}{\rho c} + 1\right)^2 + \left(\frac{X}{\rho c}\right)^2}$$

where $\alpha$ = absorption coefficient
$R$ = acoustic resistance
$X$ = acoustic reactance FIG. 4 illustrates the change in absorption coefficients α more directly by showing α versus frequency for the test specimen described in connection with FIG. 3.

Figure 5:
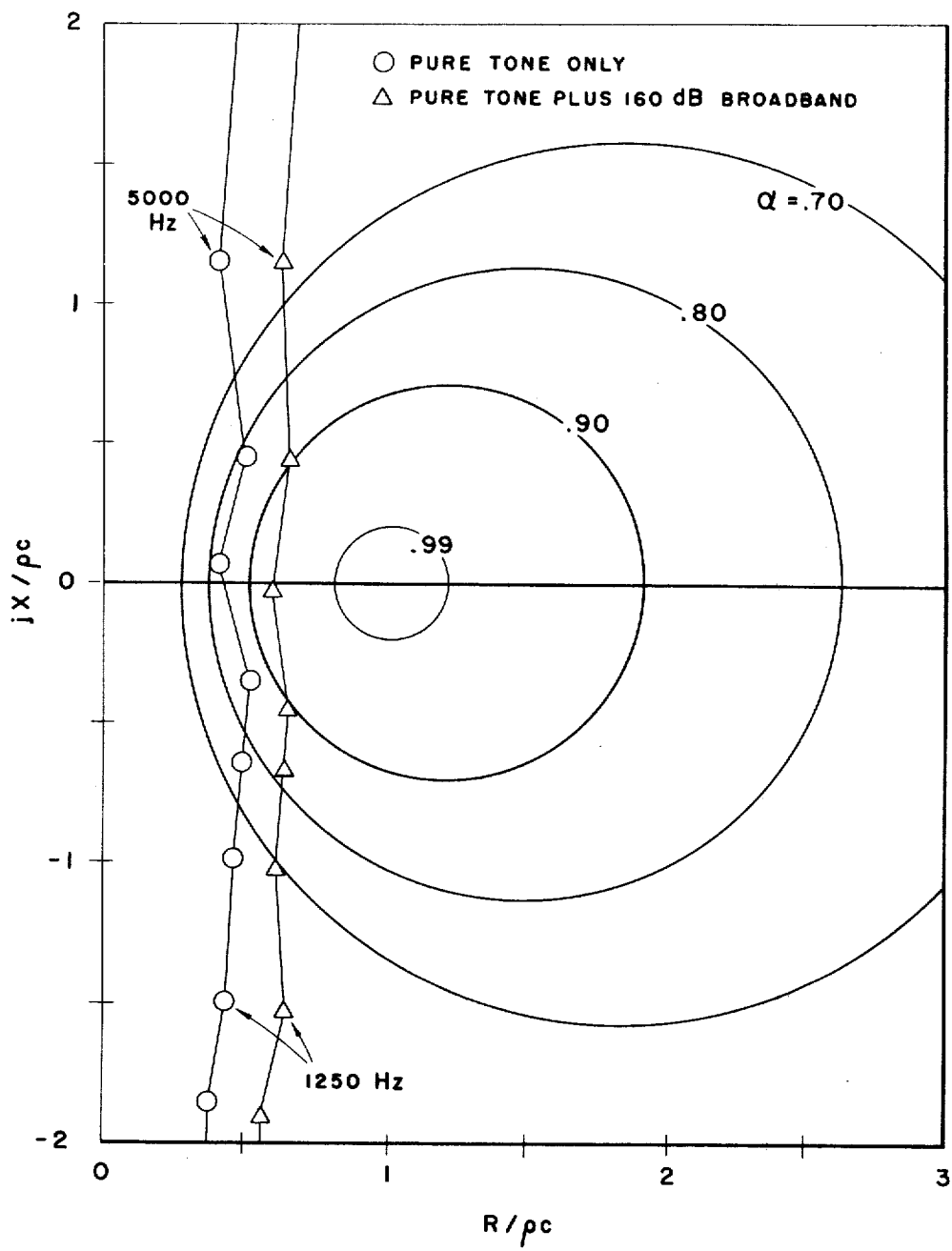
FIG. 5 is a graphic diagram illustrating an impedance plot obtained from a second test sample in accordance with the method of the invention, and the plot obtained by prior methods.
Figure 6:
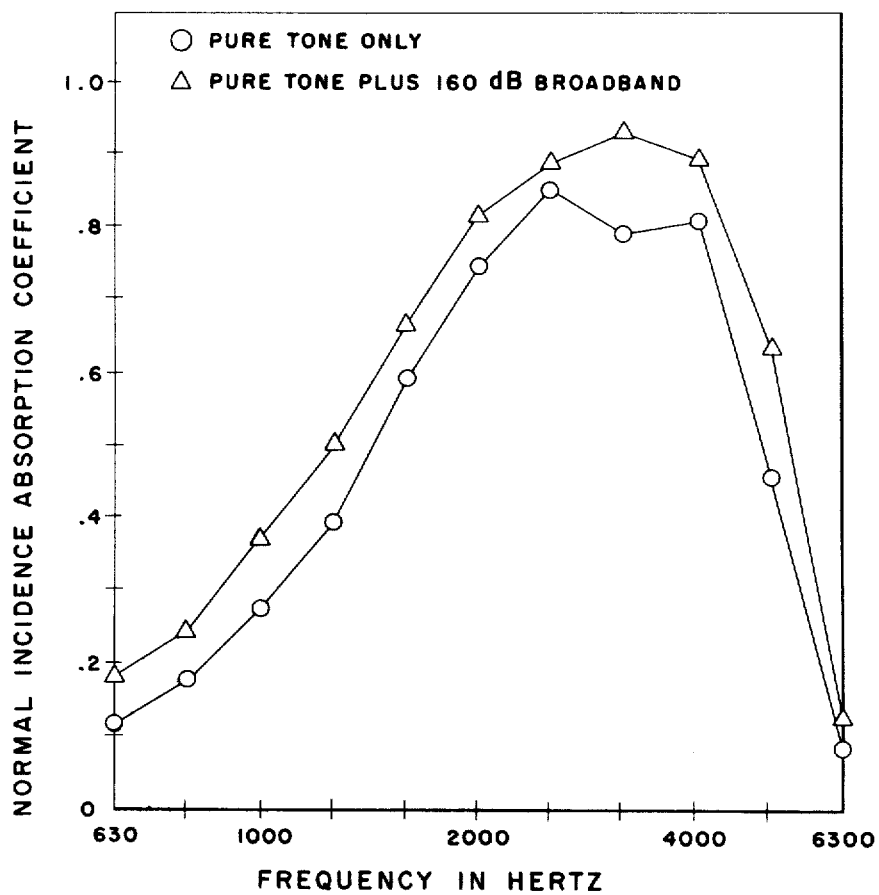
FIG. 6 is a graphic diagram illustrating the absorption coefficients of the sample referred to in FIG. 5.

FIGS. 5 and 6 show the lesser changes in impedance and absorption that are obtained with a test specimen comprising a much more linear material, namely the commercial product identified as "Feltmetal" type FM-186.

From the foregoing it will be see that the present invention, as it applies to the field of acoustics, provides a novel and improved method and apparatus for the measurement of certain acoustic phenomena. A specimen in a standing-wave tube is exposed to the combination of a low-level pure tracer tone and a broadband noise of predetermined spectral shape and level. Extraction of the tracer tone yields a measurement signal from which analysis of the sound absorption and reflection characteristics of the specimen may be obtained. In accordance with the invention the impedance of nonlinear acoustic materials has been redefined and conventional methods of measurement have been modified. The improvements attributable to the invention lead directly to the creation of new and improved sound absorbing materials and devices.

The application of the invention to the measurement of electrical impedance will now be described. The classic measurement of electrical impedance in a circuit consists essentially of a measurement of the magnitude of the voltage V, a measurement of the magnitude of the current I, and a measurement of the phase angle between the voltage and the current at some particular frequency. Thus, the basic measuring instruments comprise some form of voltmeter, ammeter, and phase meter, or their respective equivalents. Assume that it is desired to measure the input impedance at the input terminals of an unknown electrical device having an extremely nonlinear impedance. One example of such a device is an incandescent lamp. The resistance rises rapidly with temperature of the filament and hence with the current. The coiled filament also possesses some inductance, the magnitude of which depends on its geometry. The geometry, and hence the inductance, may change as a result of thermal expansion and distortion of the filament. Similar statements apply to a small capacitance component inherent in the lamp's geometry.

Figure 7:
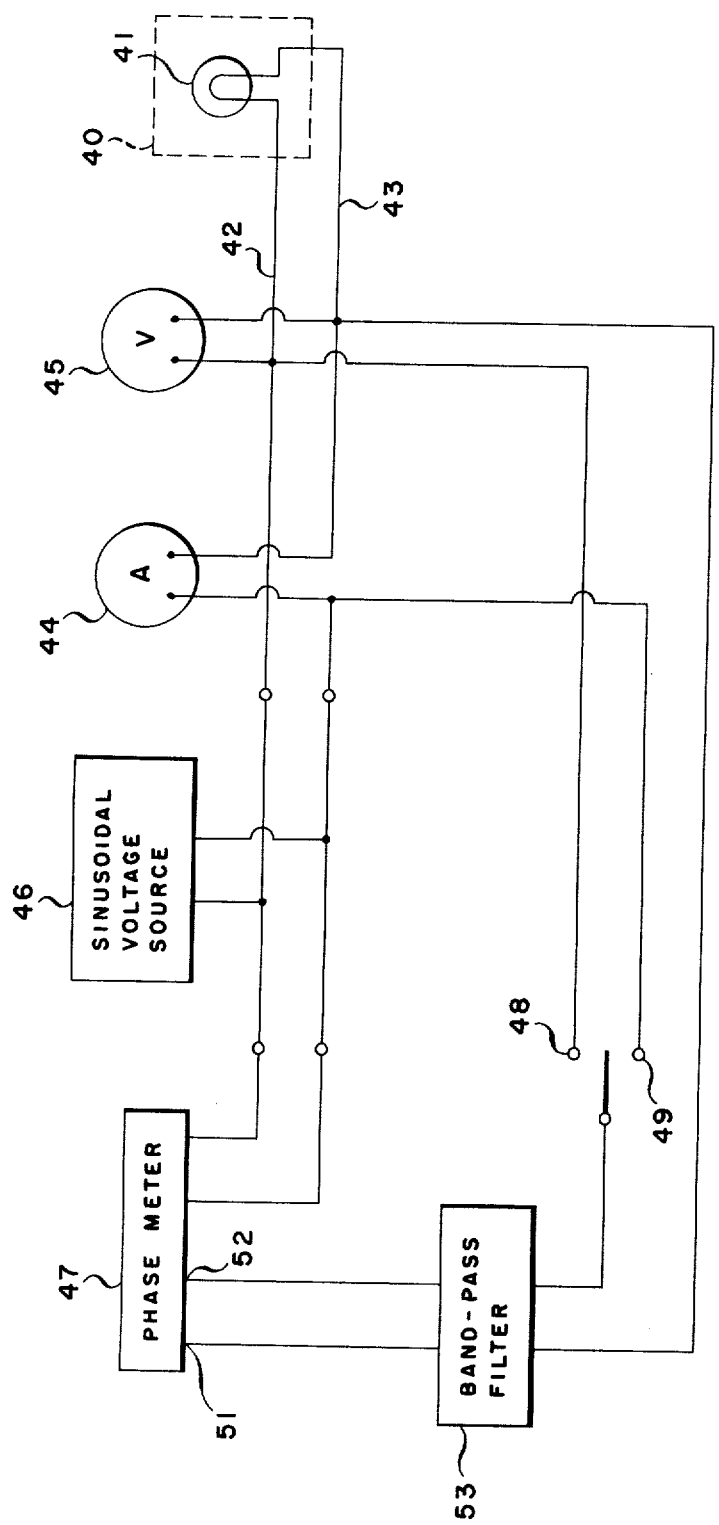
FIG. 7 is a block diagram illustrating the measurement of electrical impedance by conventional prior-art means, as is useful in the exposition of the present invention.

Referring to FIG. 7 there is shown within dotted outline 40 a device having an extremely nonlinear impedance which is to be measured. By way of example, this device (40) may comprise an incandescent lamp 41. The lamp 41 is connected via lines 42 and 43 to a conventional impedance-measuring circuit including ammeter 44 and voltmeter 45. That is, the apparatus and method illustrated in FIG. 7 is representative of the prior art and a consideration thereof is useful in the exposition of the present invention.

A source 46 of sinusoidal voltage provides an operating potential to lamp 41 via lines 42 and 43. The voltage from source 46 may be of any given frequency. Ammeter 44, which is in series with the lamp 41 and the source 46, measures the magnitude of the current supplied to the device (40). Voltmeter 45 is connected in parallel with the input of device (41) and measures the operating voltage thereat.

A phase meter 47 is used to make the necessary measurement of the phase angle between the voltage and current at the terminals of the test device 40. The phase meter may, by way of example, comprise an oscilloscope, although any suitable and well-known type of phase meter may be used. In the conventional circuit shown in FIG. 7, the voltage source 46 provides a time-based signal directly to the phase meter 47 at a given frequency. Switches 48 and 49 permit either the voltage signal or the amperage signal to be connected to the second input 51 and 52 of the phase meter 47 so that the phase between the reference input (42-43) and the test input 51-52, may be measured. Optional bandpass filter 53 is tuned to the given frequency of source 46, and is interposed between switches 48-49 and inputs 51-52 of the phase meter 47. Filter 53 is not necessary if the device 40 is linear, but it is very desirable if the test device is nonlinear, because nonlinear distortion of the current in the test device tends to produce spurious frequency components that disturb the phase measurements and cause errors in the amperage measurement. These shortcomings are overcome by the present invention.

Figure 8:
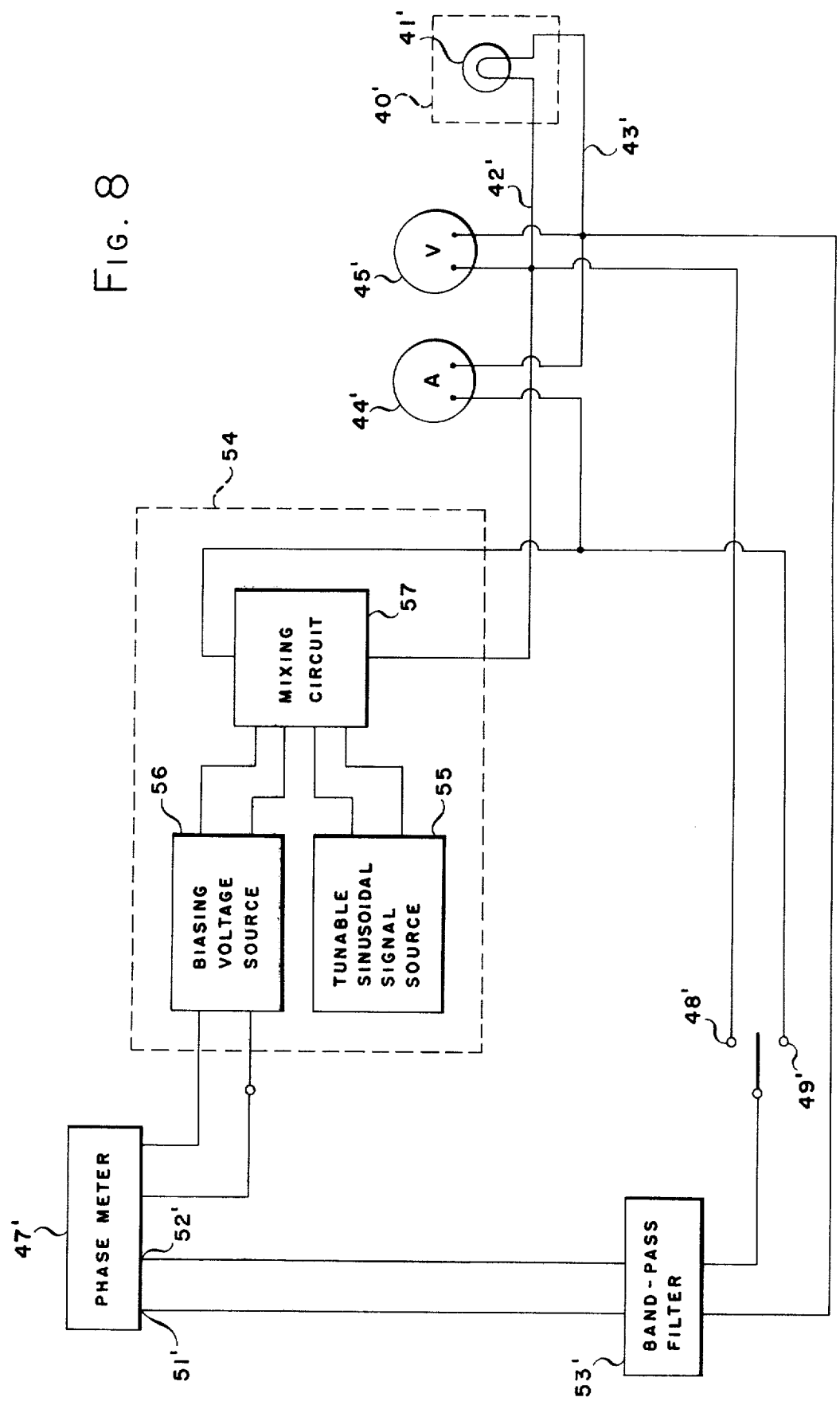
FIG. 8 is a block diagram illustrating apparatus for the measurement of electrical impedance in accordance with the present invention.

There is shown in FIG. 8 a modification of the prior art apparatus of FIG. 7, so as to include the improvement of the present invention. In accordance with the present invention, the sinusoidal voltage source 46 as shown in FIG. 7, is replaced by the circuit assembly 54 shown in FIG. 8. The remaining circuit elements of FIG. 8 correspond to their counterpart elements in FIG. 7, and are indicated by the addition of a prime (') to the previously used identifying indicia.

Circuit assembly 54 comprises a tunable sinusoidal signal generator 55 which may be selectively adjusted to provide any desired output frequency. The output of generator 55 comprises the tracer signal which is to be later extracted in the manner contemplated by the invention. Assembly 54 further includes a biasing signal voltage source 56, and a mixing circuit 57. Biasing signal source 56 produces a voltage having the same magnitude and frequency spectrum as would actually be encountered in the normal utilization of the test device 40'. That is, source 56 is the principal source of operating potential for the test device 40'. Mixing circuit 57 combines the sinusoidal voltage from generator 55 with the biasing voltage from source 56. The combined outputs energize the test device 40'.

In accordance with the underlying principle of the invention, no other circuit change to the prior art configuration of FIG. 7 is necessary beyond that shown in FIG. 8, although optimum choice of circuit components may differ. For example, the use of a biased excitation source makes it desirable to use a bandpass filter 53' having a much narrower passband than that of filter 53 (viz., the prior art), if the biasing voltage (56) contains frequency components near the output frequency of tracer signal generator 55. That is, filter 53' is closely analogous, and functionally equivalent to, the narrow-band tracking filter 22 shown in FIG. 1.

Notwithstanding the several similarities between the circuits of FIG. 7 and FIG. 8, the manner in which the conventional impedance test is made, and the manner in which the impedance test of the present invention is made, are entirely different. Suppose for example that the normal current encountered by the device 40' in its intended use contains a considerable amount of voltage having a broadband frequency spectrum. Then the source of bias noise (viz., that obtained from source 56') would be chosen to provide this same broadband voltage. Source 56' may actually comprise a broadband voltage source and a spectrum-shaping network. In the conventional tests, as accomplished by the apparatus of FIG. 7, the voltage output of the sinusoidal voltage source 46 may be adjusted to be high enough to approximate the same root-mean-square (rms) voltage as the broadband voltage. According to the present invention, however, the sinusoidal voltage from generator 55 is only a tracer signal and its level is kept low relative to the broadband signal from the output of mixing circuit 57, such that the tracer frequency (55) contributes little to the heating of the filament of lamp 41'. If the test device 40 is linear, then the conventional test is valid and one may correctly read the voltage and current from voltmeter 45 and the ammeter 44, respectively. If the test device 40 is at all nonlinear and the conventional test is attempted, then it is better to read both the voltage and current at the phase meter 47 for the reason that this arrangement senses only the signals at the given frequency of source 46 inasmuch as filter 53 has rejected the spurious signals resulting from distortion in the device 40. In this case, the voltmeter 45 and ammeter 44 might be retained in their original location merely as a means of calibrating phase meter 47 by substituting a linear dummy load instead of the test device.

In accordance with the present invention, all observations, voltage, current, and phase, must be made by means of the phase meter 47' after filtering through bandpass filter 53'. The voltmeter and ammeter readings have no direct relevance to the impedance measurement, but are useful only as an optional calibration aid as previously described.

As can be seen from the foregoing, the present invention provides an improved method and apparatus for the measurement of nonlinear impedance in electrical devices.

Figure 9:
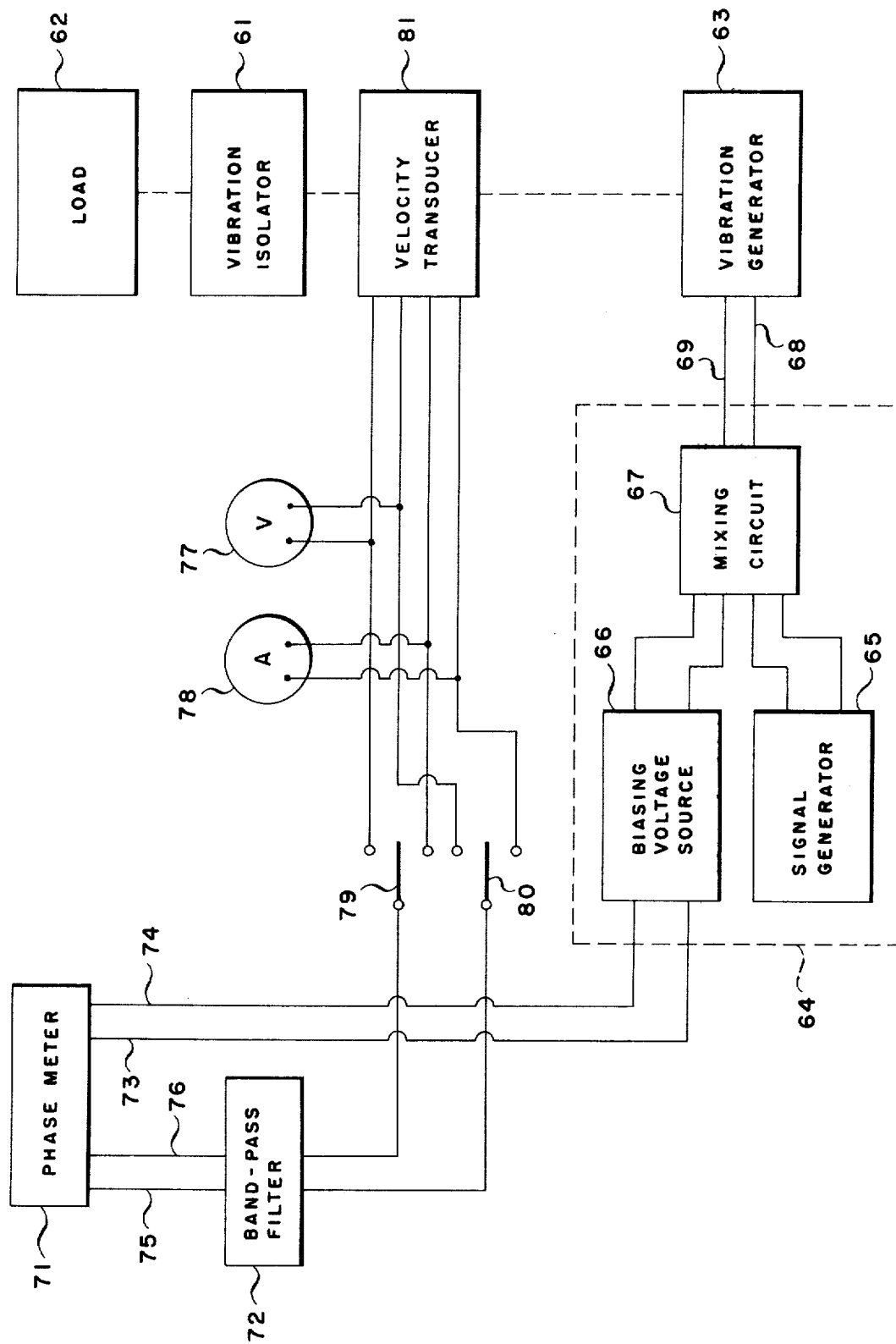
FIG. 9 is a functional block diagram illustrating apparatus for the measurement of nonlinear mechanical impedance.

With reference to FIG. 9 there will now be described the manner in which the present invention may be used for the measurement of mechanical impedance, often called "driving point" impedance. Heretofore, special transducers have been developed to facilitate the measurement of driving point impedance. Typically, these transducers comprise a compact combination of a force-sensing load cell and a velocity-sensing transducer. The combination of these two transducers provide the electrical analogs of the force and the velocity exhibited by the test device. The apparatus of FIG. 9 shows an arrangement, according to the present invention, for measuring the driving point impedance of a vibration isolator 61 which is interposed between a load 62 and a vibration generator 63. The combination of isolator 61 and load 62 comprises the test specimen. By way of example, the component of the specimen comprising vibration isolator 61 may consist of a silcone rubber vibration isolator which supports the mass of load 62. Isolator 61 is described as being made of silicone rubber since it is a good example of a material well known to have dynamic mechanical properties which vary greatly with amplitude of displacement. That is, this material is quite nonlinear and is useful in exemplifying the utility of the invention.

A conventional test of driving point impedance, conducted in accordance with the prior art would utilize a sinusoidal electrical power supply to drive an electromechanical vibration generator comprising the excitation source for the test specimen. In accordance with the prior art, a combined force and velocity transducer would be located between the specimen and the sinusoidal vibration generator. If the specimen response is linear, so as to create no distortion therein, the input force may be determined from a voltmeter connected directly to the sinusoidal power supply, and the velocity may be determined from a voltmeter connected directly to the force/velocity transducer. Phase angle may be determined from a comparison of the two voltages thus obtained. Mechanical impedance, being the ratio of force to particle velocity, can be derived from these measurements. A better practice would be to measure the force-proportional voltage and the velocity-proportional voltage, and the phase angle between them by means of an oscilloscope, having first filtered the signals through an appropriate bandpass filter. Appropriate switches may be used for alternately connecting the phase meter to the force and velocity circuits. Impedance measurements of this type are well known to those versed in the art, but are valid only if the above-mentioned assumption is true that the specimen's response is linear and there is no distortion. Practical experience has shown that this is rarely true in the real world.

In accordance with the present invention, the sinusoidal power supply to the vibration generator, as described above with reference to conventional practice, would be replaced by a circuit assembly analogous to that identified at 54 in FIG. 8. This circuit assembly 64 comprises a tunable sinusoidal signal generator 65, a biasing voltage source 66, and a mixing circuit 67. The biasing voltage source 66 is used to supply the complex signal which will produce the type and level of vibration that is expected to occur in the actual utilization of the test specimen 61-62. A smaller sinewave signal is produced by the signal generator 65 and mixed with the main signal (66) by mixing circuit 67. The combined signal appears on lines 68-69 for powering the vibration generator 63. Vibration generator 63 may be any suitable and well-known electromechanical transducer. The remainder of the measuring circuit comprises phase meter 71 and bandpass filter 72. Phase meter 71 may, as previously described, comprise an oscilloscope having a first reference input consisting of lines 73 and 74 and a second measuring input consisting of lines 75 and 76. Solely as an aid in calibrating phase meter 71, voltmeter 77 and ammeter 78, and their associated switches 79 and 80 may optionally be employed. That is, for calibration purposes, sinusoidal test signals may be applied via switches 79 and 80 in lieu of the output from transducer 81. The phase meter 71 is used to measure the voltage corresponding to force, with respect to the voltage corresponding to velocity, in terms of the phase angle between them.

The functioning of the apparatus of FIG. 9 is analogous to that described previously in connection with the apparatus of FIGS. 1 and 8. Specifically, the dynamic excitation of the test specimen into its nonlinear regime is obtained via source 66 while a tracer signal of lesser amplitude is also supplied to the specimen from generator 65. The tracer signal is extracted via filter 72 for use in making the phase angle measurement indicative of driving point impedance.

As an example of another type of impedance of a mechanical system which may be measured by the present invention, the behavior of torsional systems is also thoroughly analogous to electrical or acoustical systems. In such an analogy, torque corresponds to voltage, angular velocity corresponds to current, moment of inertia corresponds to inductance, torsional compliance to capacitance, etc. Thus, use of a torsional vibrational generator for the driving force to the test specimen, and a suitable torsional sensor and angular velocity detector may be substituted for the transducer 81 in the system of FIG. 9.

To facilitate exposition of the invention and to simplify the circuit illustrations, the configuration of the embodiments shown in FIGS. 1, 8 and 9 utilize the simplest of components. As will be appreciated by those versed in the art, many kinds of more sophisticated circuit components may be assembled to result in the system of the invention which would be functionally equivalent to the exemplary systems. More particularly, a wide variety of phase measuring instruments are available other than the oscilloscope suggested. The essential feature of the invention in all cases, whether mechanical, electrical, acoustical, or otherwise, is the provision of a biasing input excitation of the test specimen representing an actual expected operating environment for the test specimen, and the supposition thereupon of a sinusoidal sampling or tracer signal, and the recovery of the tracer signal to the exclusion of all other signals as the effective specimen-response signal. A determination of impedance is then made from these tracer signal data.

In all types of impedance measurements made in accordance with the invention, whether electrical, mechanical, acoustical, or otherwise, if the specimen is nonlinear (response not simply proportional to input amplitude) it has been discovered that the impedance measured in the presence of simulation of actual operating conditions is more useful for predicting the behavior of the system and hence is a more valid test procedure.

In summary, from the foregoing it will be seen that the present invention provides a novel and improved method and apparatus for the measurement of certain impedance phenomena of oscillatory systems. It is particularly applicable to such systems which exhibit nonlinear behavior at high excitation amplitudes. The specimen is excited by a combination of a low-intensity pure sinusoidal tracer signal and a high-intensity biasing signal having a broadband spectrum. Extraction of the tracer signal yields a measurement indicative of the real-world characteristics of the specimen.

In accordance with the invention, the impedance of nonlinear elements has been redefined and conventional methods of measurement have been modified. The improvements attributable to the invention lead directly to the creation of new and improved materials and structures. It should be understood, however, that while the invention has been described with respect to specific impedance measurements in the several physical disciplines relating to acoustical, electrical, and mechanical systems, it will be recognized by those versed in the art that it is applicable to other systems within these physical disciplines. Thus, the invention is properly considered as a generalized technique for measuring a frequency-dependent variable in a nonlinear system.

What is claimed is:

1. The method of measuring a frequency dependent variable corresponding to the ratio of force (or root-mean-square voltage) to the normal component of the particle velocity (or root-mean-square current), appearing in a system element, at a particular frequency and in the presence of a given excitation spectrum, in a nonlinear oscillatory signal transmission system, comprising the steps of:
   introducing a biasing oscillatory signal into said system at level sufficient to reach the nonlinear regime thereof;
   superimposing a test oscillatory frequency signal onto said biasing signal, the amplitude level of said test frequency signal being lower than the level of said biasing signal; and
   separating said test frequency signal from said biasing signal at the output of said system whereby the amplitude of the extracted test frequency signal corresponds to the frequency-dependent variable of said system.

2. The method defined in claim 1 wherein said biasing signal has a broadband frequency spectrum and wherein said test frequency signal has a sinusoidal waveform.

3. The method defined in claim 1 wherein the level of said test frequency signal is below the nonlinear regime of said system.

* * * * *